(12) United States Patent
Powell

(10) Patent No.: US 6,780,638 B2
(45) Date of Patent: Aug. 24, 2004

(54) CELL CULTURE APPARATUS

(76) Inventor: Alexander Robert Powell, 82 Belmont Street, Southport, Merseyside (GB), PR8 1JH (*) Notice: Subject to any disclaimer, the term of this patent is extended or adjusted under 35 U.S.C. 154(b) by 147 days.

(21) Appl. No.: 10/045,665

(22) Filed: Oct. 23, 2001

(65) Prior Publication Data

US 2002/0086418 A1 Jul. 4, 2002

(30) Foreign Application Priority Data

Oct. 24, 2000 (GB) .............................................. 0025957
Nov. 1, 2000 (GB) .............................................. 0026661

(51) Int. Cl.$^7$ .............................................. C12M 1/10
(52) U.S. Cl. .............................. 435/298.2; 435/304.1
(58) Field of Search ......................... 435/298.1, 298.2, 435/297.5, 304.1–304.3; 422/102; 215/309; 222/478

(56) References Cited

U.S. PATENT DOCUMENTS

| | | | | |
|---|---|---|---|---|
| 2,100,610 A | * | 11/1937 | Paisley et al. ................. | 55/505 |
| 2,500,199 A | * | 3/1950 | Nesset .......................... | 604/407 |
| 2,605,021 A | * | 7/1952 | Churchill et al. .......... | 222/153.03 |
| 3,139,224 A | * | 6/1964 | Bloom ......................... | 222/478 |
| 3,540,700 A | | 11/1970 | Freedman et al. | |
| 3,732,149 A | | 5/1973 | Santero | |
| 3,827,943 A | | 8/1974 | Mann | |
| 3,847,749 A | | 11/1974 | Smith et al. | |
| 5,301,845 A | * | 4/1994 | Labonte ....................... | 222/211 |

FOREIGN PATENT DOCUMENTS

| | | |
|---|---|---|
| EP | 0775196 | 3/1999 |
| WO | WO 96/05285 | 2/1996 |

* cited by examiner

Primary Examiner—William H. Beisner
(74) Attorney, Agent, or Firm—Ware, Fressola, Van der Sluys & Adolphson LLP

(57) ABSTRACT

A cell culture apparatus comprises a rotor releasably housing a plurality of cell culture vessels/roller bottles. The apparatus provides for rotation of the rotor at a controlled speed about a substantially horizontal axis and for the rotational axis of the rotor and the bottles housed therein to be tilted to a substantially vertical position in order to allow fluid to be supplied or drain therefrom. Each vessel is provided with a cap equipped with a fluid supply/drain connection arranged at the lowest point of the cap when the vessel is vertically inverted (as shown in FIG. 1). The supply/drain connection of each bottle cap is connected to a manifold that allows the supply or extraction of fluid via a sealable external connection. Venting of the gas space within the bottle during fluid transfer is provided by a snorkel tube passing upwards through the fluid, and formed as an internal extension of the bottle cap. The snorkel tube is provided with a micro-porous filter, venting to atmosphere. During cell incubation stages, the assembly of vessels is rotated about a horizontal axis in the known manner.

5 Claims, 5 Drawing Sheets

US 6,780,638 B2

CELL CULTURE APPARATUS

BACKGROUND OF THE INVENTION

1. Technical Field

This invention relates to cell culture apparatus for growing animal cells in rotating cylinders, or roller bottles.

2. Description of the Background Art

There are a variety of existing types of apparatus in which cells are cultured whilst attached to the interior of substantially horizontally mounted cylinders or bottles which are slowly rotated to ensure that all the cells are regularly bathed in culture media.

In order to increase the productivity of the apparatus, a plurality of bottles or cylinders may be connected together via a common fluid supply/extraction manifold thus allowing fluid to be transferred into or out of a number of vessels simultaneously.

It is essential in such a system to ensure that each vessel is provided with an equal volume of fluid during processing operations. In some systems, for example, U.S. Pat. No. 3,847,749, or WO 96/05285 (EU 0775196), equal fluid distribution is accomplished by means of a multi-channel peristaltic pump, with each vessel being assigned one channel of the pump. Such systems allow the bottles to processed in situ and in the horizontal position.

In other systems, for example U.S. Pat. No. 3,827,943, or U.S. Pat. No. 3,732,149 a drum or rotor housing a plurality of interconnected cylindrical vessels is tilted into the vertical position during fluid transfer operations, thus allowing the fluid level in each vessel to equalize by gravity. This has the advantage of simplicity over systems that require a separate pumping channel for each vessel. Unfortunately, the existing arrangements of tilting rotor devices require air and fluid connections to be provided at opposite ends of the vessels, and cannot therefore utilize conventional roller bottles which are readily available, sterile irradiated, in standardized sizes. It would be advantageous if this type of apparatus could be adapted to utilize standard roller bottles.

SUMMARY OF THE INVENTION

Accordingly a first aspect of the present invention provides cell culture apparatus comprising a rotor releasably housing a plurality of cell culture vessels/roller bottles and with means provided to allow rotation of the rotor at a controlled speed about a substantially horizontal axis for cell incubation purposes, with further means provided to allow the rotational axis of the said rotor and bottles housed therein to be tilted to a substantially vertical position such that a cap end of the bottles is lowermost, each bottle being provided with a cap equipped with a fluid supply/drain connection arranged at the lowest point of the cap when said bottle is disposed inverted with the cap lowermost, a manifold with one or more sealable external connections and a plurality of connections communicating with the fluid supply/drain connection of each bottle cap, with venting of the gas space within the bottle during fluid transfer being provided by means of a snorkel tube passing upwards through fluid in the inverted position and formed as an internal extension of the bottle cap, said snorkel tube extending into the body of the bottle and having an end opening into the body of the bottle at a position clear of fluid in the bottle in either the substantially vertical or horizontal directions thereof, the said snorkel tube being further provided with microporous venting means to atmosphere, the arrangement of the parts being such that fluid transfer into or out of the bottles is accomplished via the said manifold external connection whilst the rotor and bottles are in the substantially vertically inverted position.

Another aspect of the invention provides a roller bottle cap, adapted to allow fluid transfer into or out of a roller bottle whilst said bottle is inverted substantially vertically, comprising a fluid supply/drain connection arranged at the lowest point of the cap when said bottle is vertically inverted, with venting of the gas space above the fluid during fluid transfer being provided by means of a snorkel tube extending upwards through the fluid, said snorkel tube having an end opening into the body of the bottle at a position clear of the fluid therein.

More particularly, the snorkel tube is arranged to extend substantially along the central longitudinal axis of the bottle.

Preferably the snorkel tube is provided with graduations along the length thereof to indicate the volume of fluid contained within the bottle when orientated vertically. Preferably the end of the snorkel opening into the bottle is provided with a fluid trap.

BRIEF DESCRIPTION OF THE DRAWINGS

The invention will now be described by way of example with reference to the following drawings, in which.

DETAILED DESCRIPTION OF THE INVENTION

Figure 1:
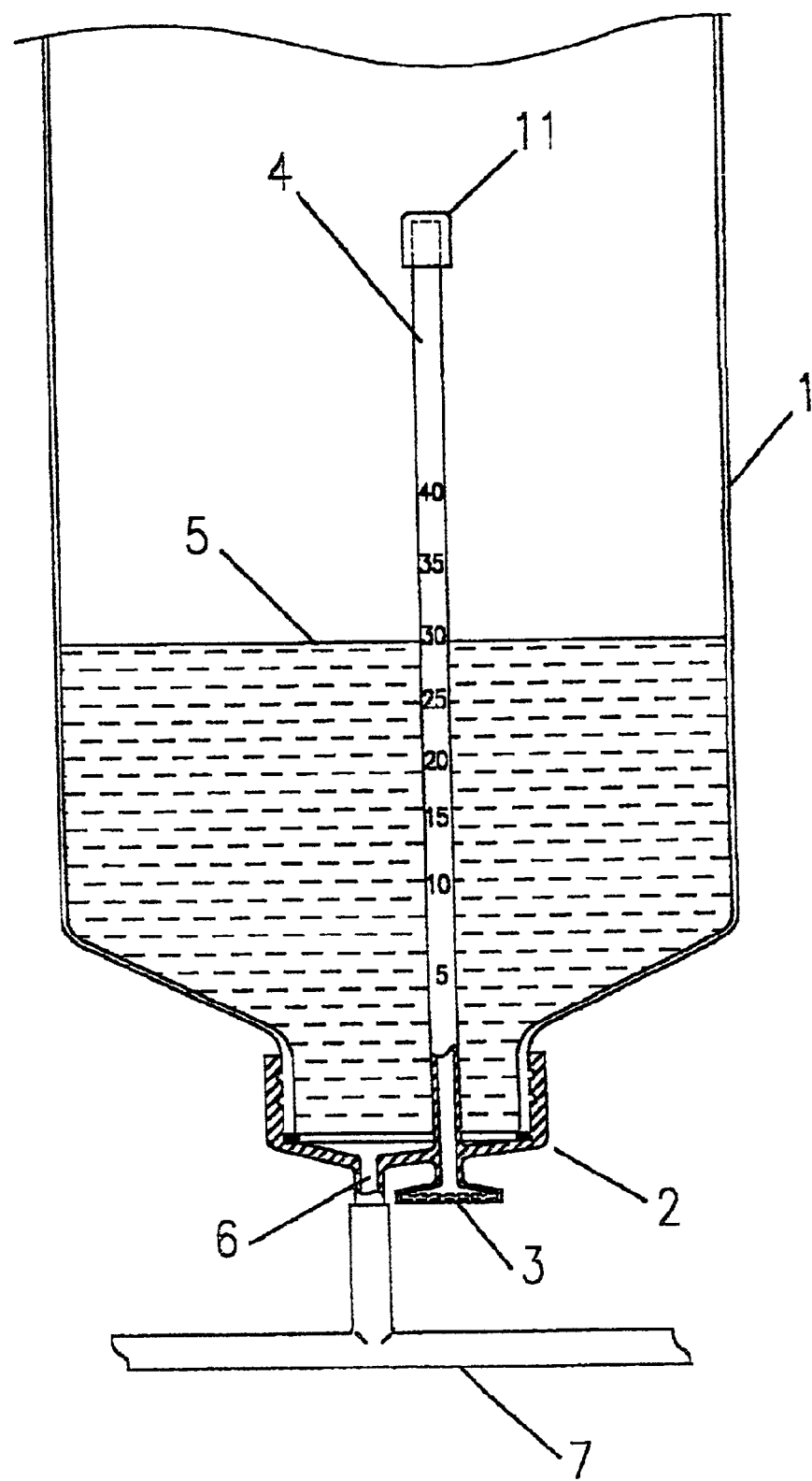
FIG. 1 shows a cell culture vessel/roller bottle in the vertically inverted position, as would be the case during fluid transfer into or out of the bottle.

Referring to FIG. 1, a cell culture vessel/roller bottle, 1 is provided with a screw fitting cap 2. The end cover of the cap 2, is formed internally as an inverted cone with a drain connection 6 provided at the apex, or lowest point, such that fluid 5 may be completely drained from the bottle whilst it is vertically inverted as shown. Fluid supply to, or extraction from, the bottle 1, is facilitated via a fluid supply/extraction manifold 7, communicating with the drain connection 6.

During fluid transfer operations into or out of the bottle 1, venting of the gas space above the fluid 5 is facilitated by means of a snorkel tube 4, substantially on the central axis of the bottle 1, and passing upwards through the fluid 5. The snorkel tube 4 is fitted with micro-porous filtering means 3 to prevent air-born contamination entering the vessel. The snorkel tube 4 may be provided with graduations, as shown, to indicate the fluid volume contained within the bottle. The inner end of the snorkel tube 4 may be further provided with a fluid trap 11 to prevent fluid splashes from entering the snorkel tube 4, during handling of the bottle.

During cell incubation stages, the roller bottle is turned to the horizontal position and rotated slowly, in the normal manner.

Figure 2:
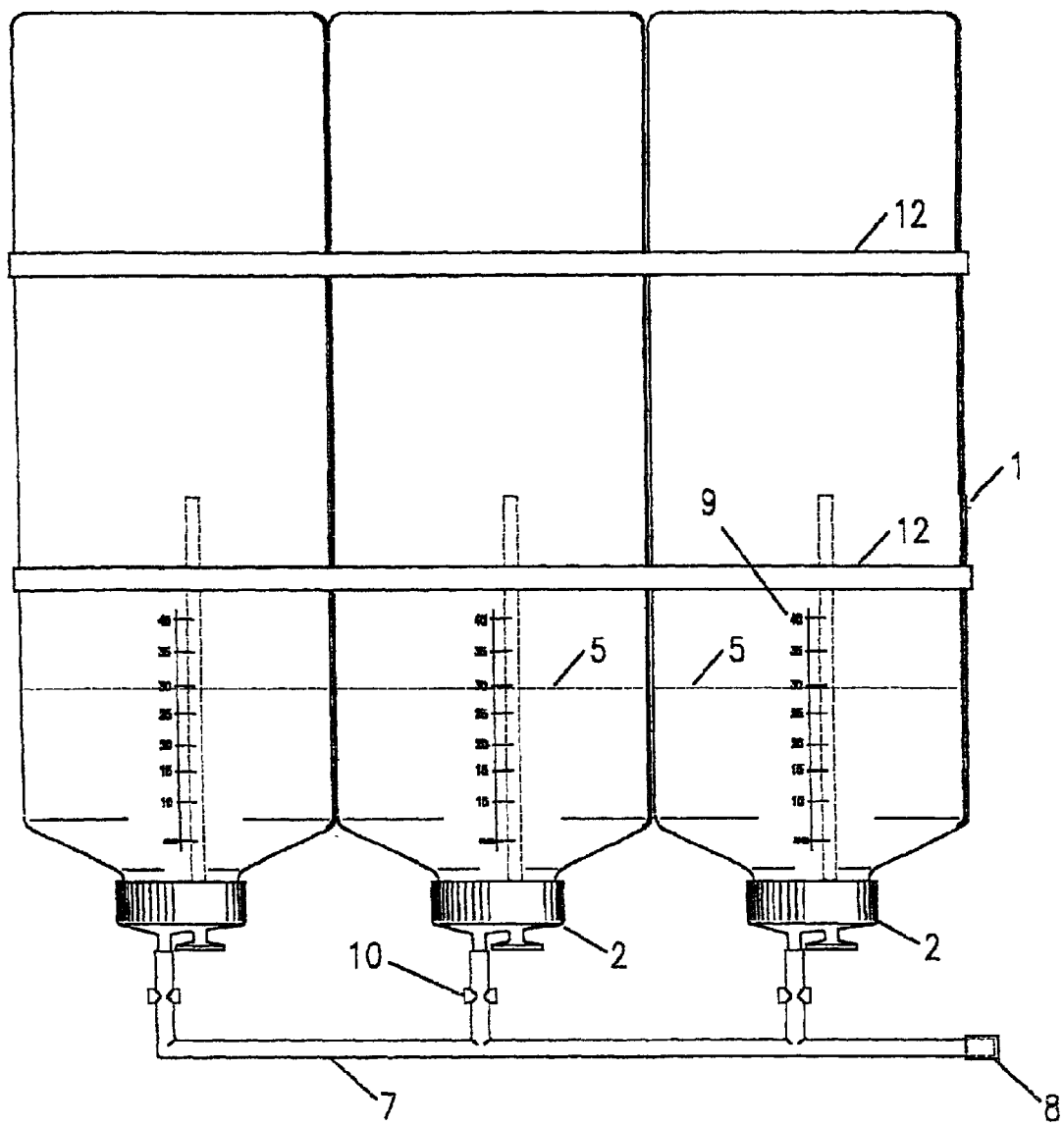
FIG. 2 shows an assembly of bottles and caps with interconnecting manifold and a sealable external connection.

Referring now to FIG. 2, a plurality of caps 2 and bottles 1 may be connected together via a common fluid supply/extraction manifold 7, and the manifold 7 provided with a sealable external connection 8. The bottles 1 are arranged with their central axis parallel, and may be secured together into a stack or assembly, by for example binding straps 12.

During fluid transfer operations, the stack of bottles is vertically inverted, as shown in FIG. 2. Equal distribution of fluid to all bottles is then assured by equalization of the fluid 5 level via the manifold 7 under the effect of gravity. As an alternative to volume graduations on the snorkel tube as described above, the bottles 1 may be provided with externally printed graduations 9, showing the fluid volume contained therein when the bottle is inverted.

During cell incubation stages, the bottle stack or assembly, is turned to the horizontal position and may be located within a drum, or rotor and rotated bodily about a horizontal axis in the known manner. In these circumstances, clamps or valves 10 may be provided to prevent siphoning of fluid between bottles whilst the stack or bottle assembly is being tilted between the vertical and horizontal positions.

It may be convenient to provide a sterile disposable assembly comprising a plurality of interconnected caps, a manifold and a sealable external connection. Roller bottles can then be fitted to the cap/manifold assembly, prior to use.

It may further be convenient to provide a sterile disposable assembly comprising a plurality of interconnected caps, a manifold, and a sealable external connection, with the roller bottles already fitted. This provides an advantage in that it eliminates the need to assemble the caps, manifold and bottles under sterile conditions prior to using the system, and thus substantially reduces the risk of contamination during the set up procedure.

Where a plurality of caps and bottles are connected together, it may be convenient to provide a single microporous vent filter to atmosphere, (not shown) communicating with each bottle cap snorkel tube 4 via a multi-way vent manifold, (not shown), rather than providing a separate vent filter for each bottle cap.

Figure 3:
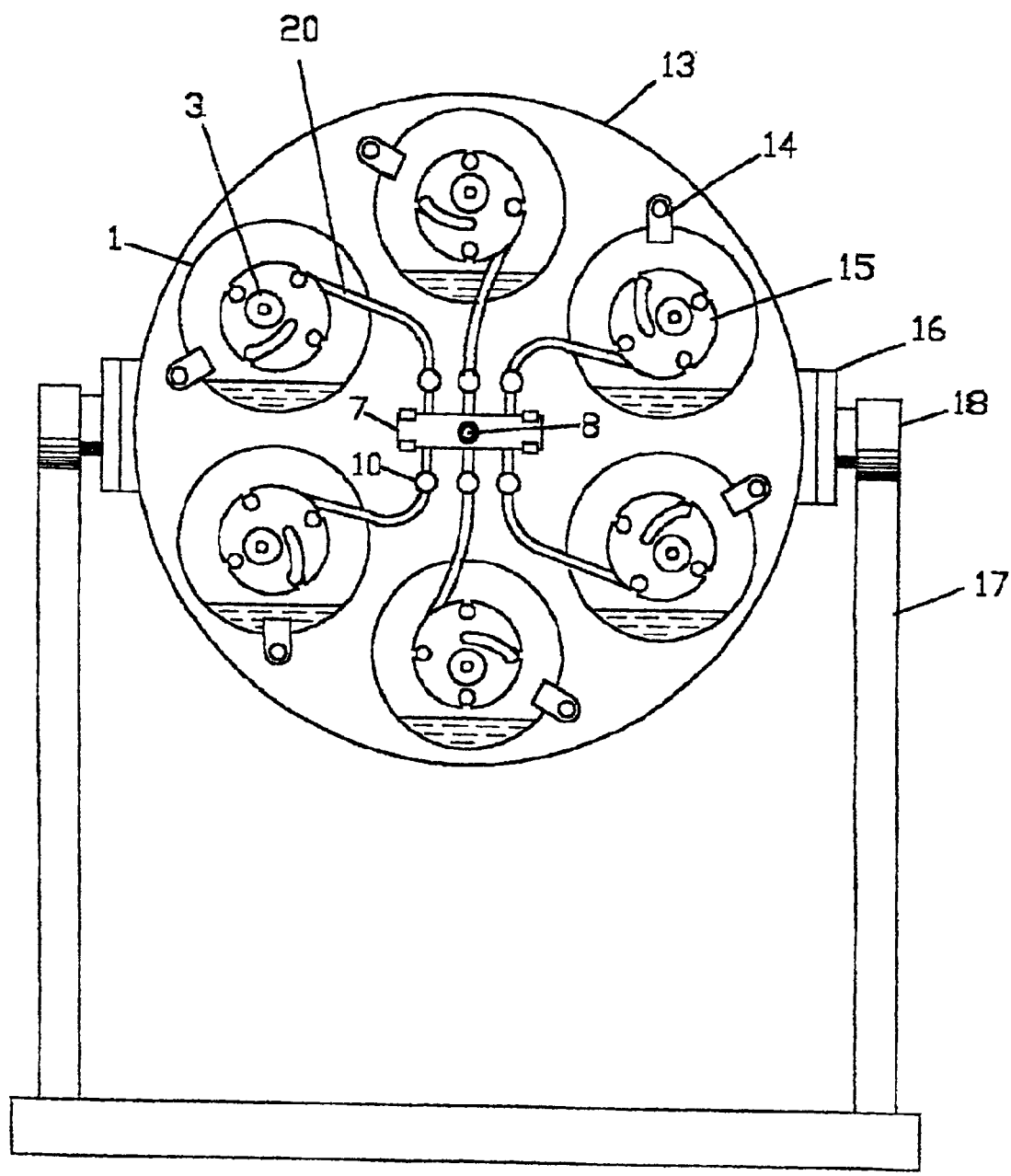
FIG. 3 shows a front view of an apparatus with the rotor in the horizontal cell incubation position, said apparatus being adapted to allow individual bottles to be removed for inspection during cell culture stages.
Figure 4:
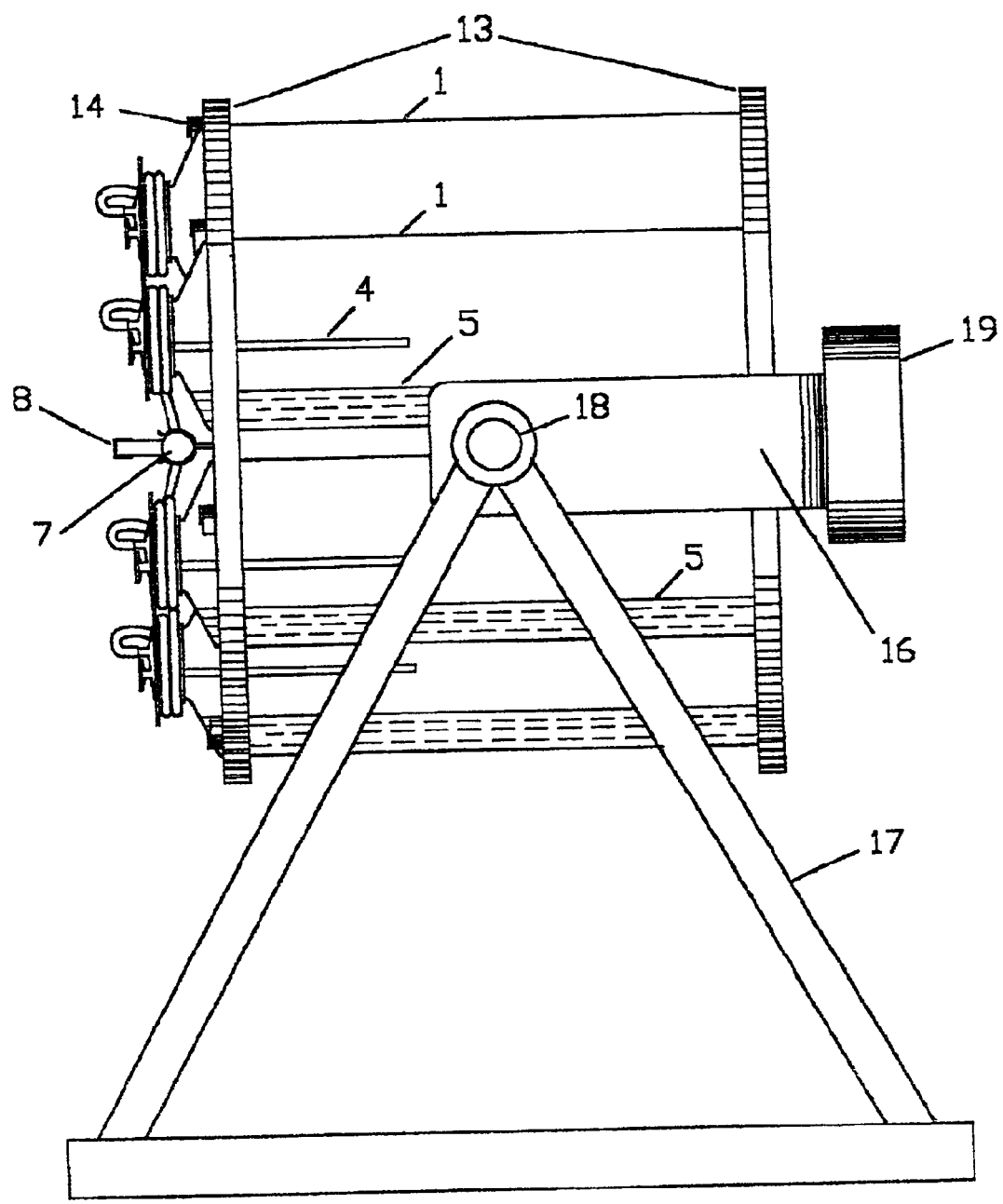
FIG. 4 shows a side view of the apparatus with the rotor in the horizontal cell incubation position.

Referring now to FIGS. 3 and 4, an embodiment of the invention is shown which is adapted to allow the bottles 1 to be removed individually for inspection during cell incubation stages. The apparatus is shown with the rotor in the horizontal cell incubation position.

A plurality of bottles 1 are housed within a rotor 13, and releasably secured by means of retaining catches 14. In order to prevent rotation of the bottles 1 relative to the rotor 13, the catch 14 may be arranged so as to engage with one or more indentations (not shown) in the shoulder of the bottle 1. A manifold 7, equipped with a sealable external connection 8 is releasably secured to the rotor 13, and communicates with the supply/drain connection of each bottle 1 by means of flexible interconnecting tubes 20. The length of each tube 20 is sufficient to allow the bottles 1 to be removed from the rotor 13, the excess length of the tubing being stored the rest of the time by being wound around the caps 15 in the manner previously revealed in EU 0775,196.

During cell incubation stages, the rotor 13 is rotated about the horizontal axis at a controlled speed by motor-gear unit 19 and a speed controller (not shown).

The rotor 13 is mounted upon a tilting frame 16, that may be rotated about pivot bearings 18, which are mounted upon a supporting frame 17. The tilting frame 16 may be locked in the vertical or horizontal position by locking means not shown. The interconnections 20 between each bottle 1 and the manifold 7 may be provided with valves 10, to prevent fluid siphoning between the bottles 1 when the tilting frame 16 and rotor 13 are in intermediate positions between vertical and horizontal.

Figure 5:
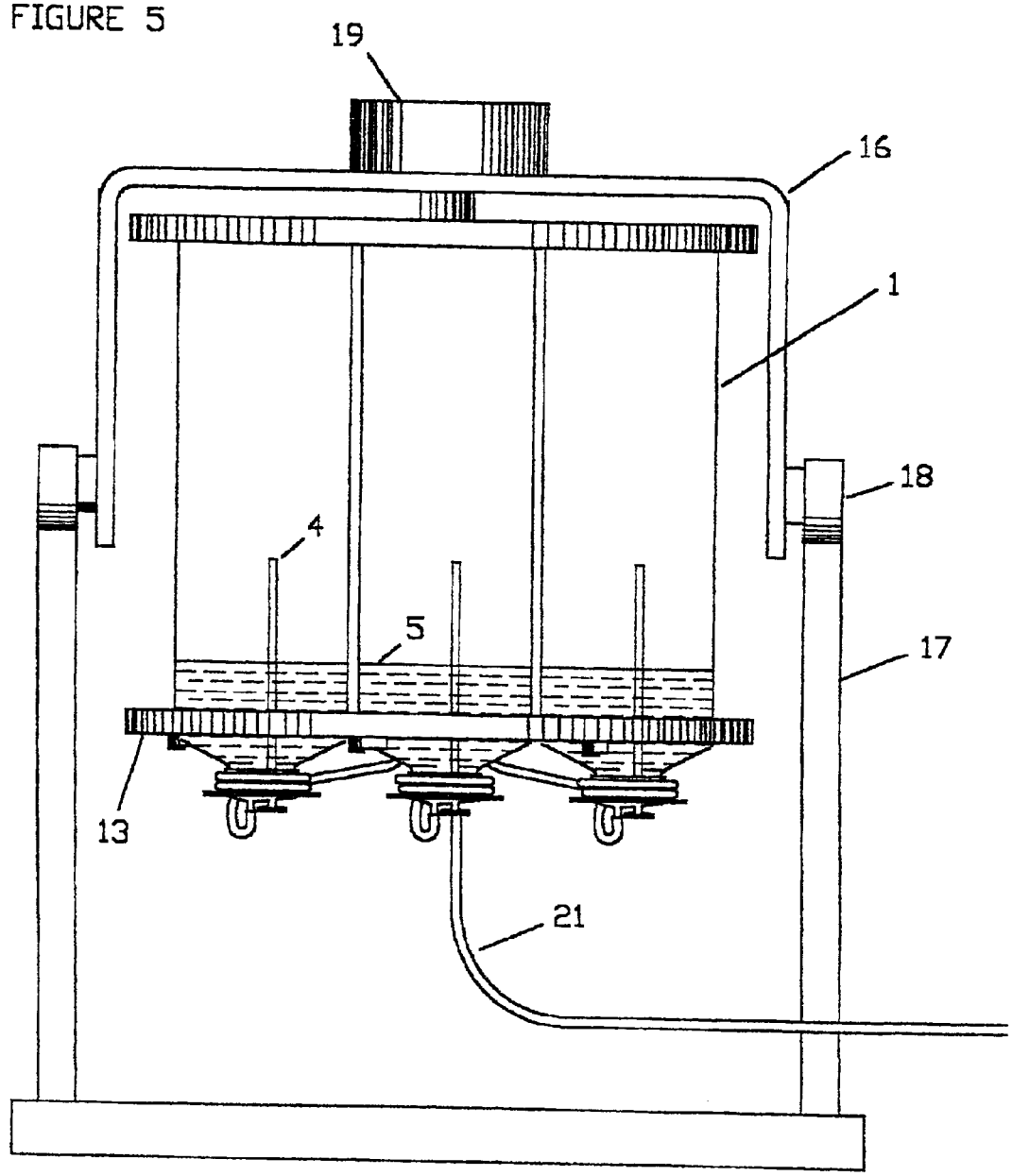
FIG. 5 shows a front view of the apparatus with the rotor in the vertical position to allow fluid transfer into or out of the bottles.

Referring now to FIG. 5, a front view of the apparatus is shown, with the rotor 13 and tilting frame 16 in the vertical position to facilitate fluid transfer into or out of the bottles 1. Fluid is transferred by means of an umbilical 21, that is connected aseptically to the sealable external connection 8 (FIGS. 3 & 4), and by pumping means (not shown), or by gravity head from a receiver (not shown).

As fluid is transferred into or out of the bottles 1, the gas space above the fluid 5 is vented to atmosphere via the snorkel tubes 4. Equal distribution of fluid 5 between bottles 1 is assured by allowing the levels to equalize under gravity and by equalization of the pressure within the gas space above the fluid 5 by snorkel tubes 4.

What is claimed is:

1. Cell culture apparatus comprising a rotor releasably housing a plurality of cell culture vessels/roller bottles and with means provided to allow rotation of the rotor at a controlled speed about a substantially horizontal axis for cell incubation purposes, with further means provided to allow the rotational axis of the rotor and bottles housed therein to be tilted from a substantially horizontal position to a substantially vertical position such that the bottles are in an inverted position with cap ends of the bottles lowermost, each bottle having a body and being provided with a cap on its cap end, each cap being equipped with a fluid supply/drain connection arranged at a lowest point of the cap when the bottle is in the inverted position, a manifold with at least one sealable external connection and a plurality of connections communicating with the fluid supply/drain connection of each bottle cap, each bottle having a snorkel for venting of gas space within the bottle during fluid transfer, each snorkel tube passing upwards through any fluid in its respective bottle when in the inverted position and formed as an internal extension of the cap thereon, each snorkel tube extending into the body of its respective bottle and having an end opening into the body of the bottle at a position clear of any fluid in both the bottle in the substantially vertical and horizontal orientations thereof, each snorkel tube being further provided with miro-porous venting means to atmosphere, whereby fluid transfer into or out of the bottles is accomplished via the at least one external connection of the manifold whilst the bottles are in the inverted position.

2. Cell culture apparatus as claimed in claim 1 in which each snorkel tube is arranged to extend substantially along a central longitudinal axis of its respective bottle.

3. Cell culture apparatus as claimed in claim 1 in which each snorkel tube is provided with graduations along a length thereof.

4. Cell culture apparatus as claimed in claim 1 in which an end of each snorkel tube opening into its respective bottle is provided with a fluid trap.

5. Cell culture apparatus as claimed in claim 1 in which a respective clamp or valve is provided in said manifold between the respective bottle cap fluid supply/drain connections.

* * * * *